United States Patent
Fan (10) Patent No.: US 6,544,164 B1
(45) Date of Patent: Apr. 8, 2003

(54) LIGHT WAVE ENERGY HEALTH MAGNETIC RING

(75) Inventor: James Fan, Taipei (TW)

(73) Assignee: Jamie Life International Co., Ltd., Taipei (TW)

( * ) Notice: Subject to any disclaimer, the term of this patent is extended or adjusted under 35 U.S.C. 154(b) by 0 days.

(21) Appl. No.: 09/986,829

(22) Filed: Nov. 13, 2001

(51) Int. Cl.[7] ............... A61N 1/00; A44C 7/00
(52) U.S. Cl. .................... 600/15; 63/12
(58) Field of Search ............... 600/9, 15, 13; 7/169; 63/12, 14.5, 29.2; 24/303; 724/183

(56) References Cited

U.S. PATENT DOCUMENTS

| | | | |
|---|---|---|---|
| 3,943,912 A | 3/1976 | Nakayama | 600/15 |
| 4,095,587 A | 6/1978 | Ishikawa | 600/15 |
| 4,905,335 A | 3/1990 | Tervola | 7/169 |
| 4,912,944 A | 4/1990 | Crosley et al. | 63/29.2 |
| 5,036,681 A | 8/1991 | Schaerer | 63/14.5 |
| 5,137,507 A | 8/1992 | Park | 600/13 |
| 5,333,767 A | 8/1994 | Anderson | 224/183 |
| 5,349,725 A | 9/1994 | Levy | 24/303 |
| 5,432,986 A | 7/1995 | Sexton | 24/303 |
| 5,827,170 A | 10/1998 | Gebran | 600/15 |
| 5,989,178 A | 11/1999 | Chiu | 600/15 |
| 6,048,301 A | 4/2000 | Sabuda | 600/9 |

OTHER PUBLICATIONS

FDP Magnetics; Registered 2000–2002; www.fdp-magntics.com; pp. 1–3.

Primary Examiner—Eric F. Winakur
Assistant Examiner—Nikita R Veniaminov
(74) Attorney, Agent, or Firm—Leong C. Lei (57) ABSTRACT

A light wave energy health magnetic ring includes a plurality of blocks of different shapes formed from superconductive magnetic materials, natural crystals containing strong natural magnetic fields, and infrared ceramic beads. Bottom portions of the superconductive magnetic materials are formed with recesses for embedding crude crystals therein. Round, flat and circular-shaped, or wheel-shaped natural crystals and ceramic beads are spacedly disposed between adjacent superconductive magnetic materials such that the natural crystals are arranged in diagonally opposite positions. These elements are connected in a ring shape for wearing by a user. The magnetic waves can penetrate the muscles and bones of the body of the user to magnetize the cells of the body to thereby improve the circulation functions of the body.

6 Claims, 9 Drawing Sheets

LIGHT WAVE ENERGY HEALTH MAGNETIC RING

BACKGROUND OF THE INVENTION

1. Field of the Invention

This invention is related to a light wave energy health magnetic ring which includes a plurality of superconductive magnetic materials of different shapes, natural crystals and ceramic beads connected in a ring shape for wearing by a user. The magnetic properties of the superconductive magnetic materials are employed to magnetize the cells of the human body to thereby improve circulation functions. The natural crystals and ceramic beads disposed between the superconductive magnetic materials can stabilize the magnetic field.

2. Description of the Prior Art

The basic units of all living creatures are cells, which are made up of protein, fat, sugar, phosphor, calcium and water. The cell surface is magnetic, and electromagnetic action takes place on the cell surface. The chemical components, due to the inter-attraction and repulsion of electrons, work together to make the cells active to perform physiological functions. The amount of electrons affects the activity of the cells. New cells contain the largest amount of electrons. Old cells produce bubbles and therefore contain fewer electrons. Cells like blood cells, muscles, bone marrow, etc., are also counted in terms of the number of electrons. Therefore, when a person has cells containing insufficient electrons and is weak, according to Fleming's right-hand rule, magnetization can cause the cells per se to produce electric power by cutting the magnetic field via a conductor.

SUMMARY OF THE INVENTION

The primary object of the invention is to provide a light wave energy health magnetic ring, which includes a plurality of superconductive magnetic materials of different shapes, natural crystals and ceramic beads connected in a ring shape for wearing by a user. The magnetic properties of the superconductive magnetic materials are employed to magnetize the cells of the human body to thereby improve circulation functions. The natural crystals and ceramic beads disposed between the superconductive magnetic materials can stabilize the magnetic field.

In the aforementioned magnetic ring, round or flat and circular shaped or wheel-shaped natural crystals and ceramic beads are arranged between the superconductive magnetic materials, and the natural crystals are disposed in diagonally opposite positions.

In the aforementioned magnetic ring, a recess is formed in each of the superconductive magnetic materials to receive a crude crystal so that the superconductive magnetic materials cooperate with the crude crystals to produce a whirling magnetic field to enhance the magnetizing effect.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
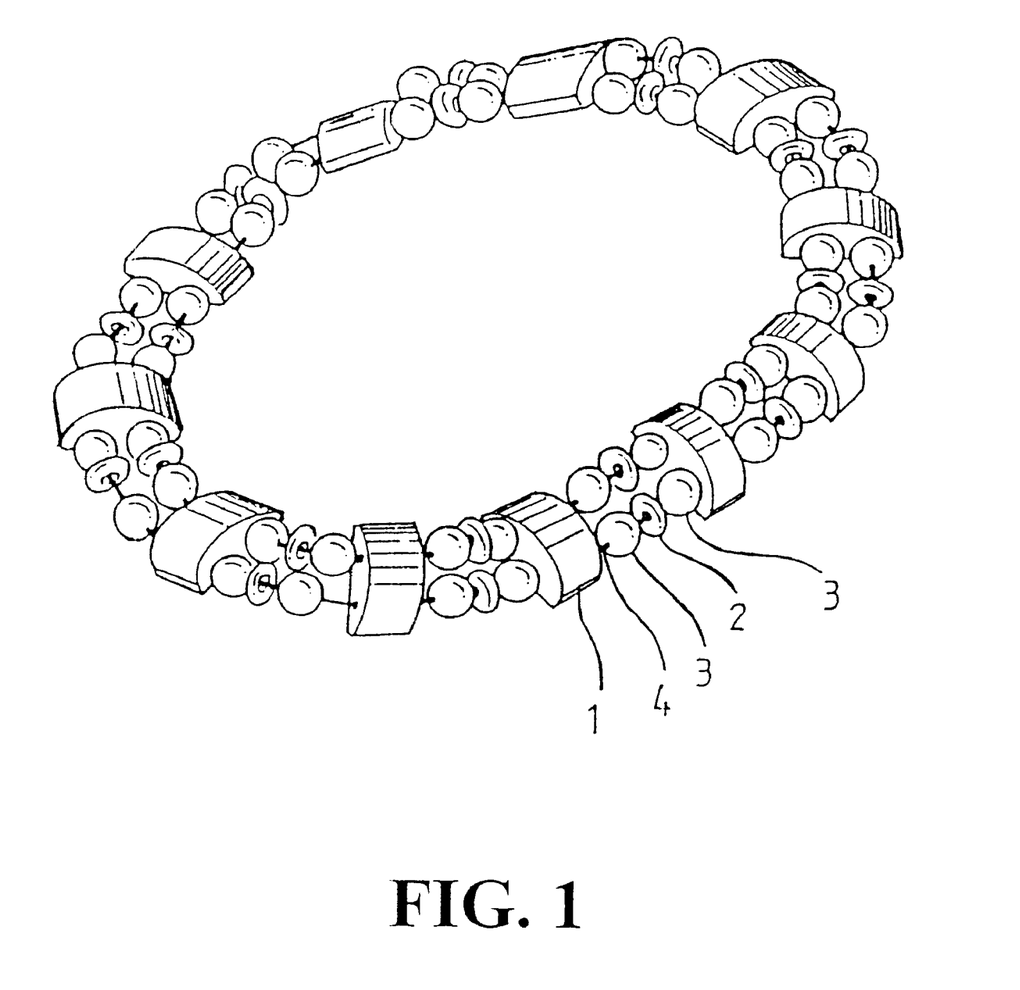
FIG. 1 is a schematic perspective view of the invention.
Figure 2:
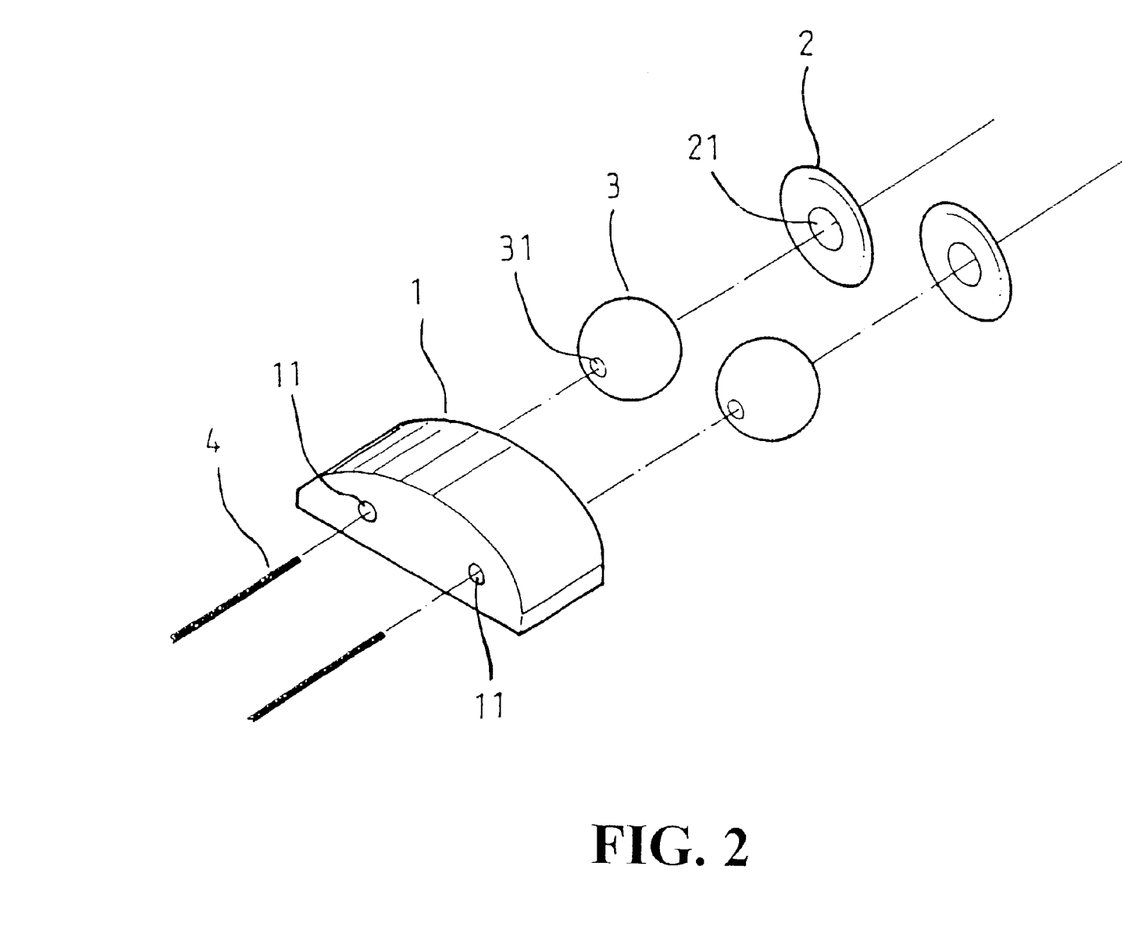
FIG. 2 is a schematic exploded view of the invention in part.

Referring to FIGS. 1 and 2, the present invention includes blocks formed from superconductive magnetic materials 1 of different colors. The superconductor magnetic materials 1 are spacedly arranged according to the same or different polarities. Between adjacent superconductive magnetic materials 1 is disposed a wheel-shaped powerful natural crystal 2, with two ceramic beads 3 disposed on both sides of the crystal 2. An elastic string 4 passes through two through holes 11 in the superconductive magnetic material 1, a center hole 21 in the crystal 2, and through holes 31 in the ceramic beads 3 to connect these elements in a ring shape for wearing. Due to the difference in polarity arrangement, magnetic waves of the superconductive magnetic materials 1 of different colors can pass through the human body to magnetize the cells to thereby improve the micro-circulation function of the human body and the physique of the human body.

Figure 3:
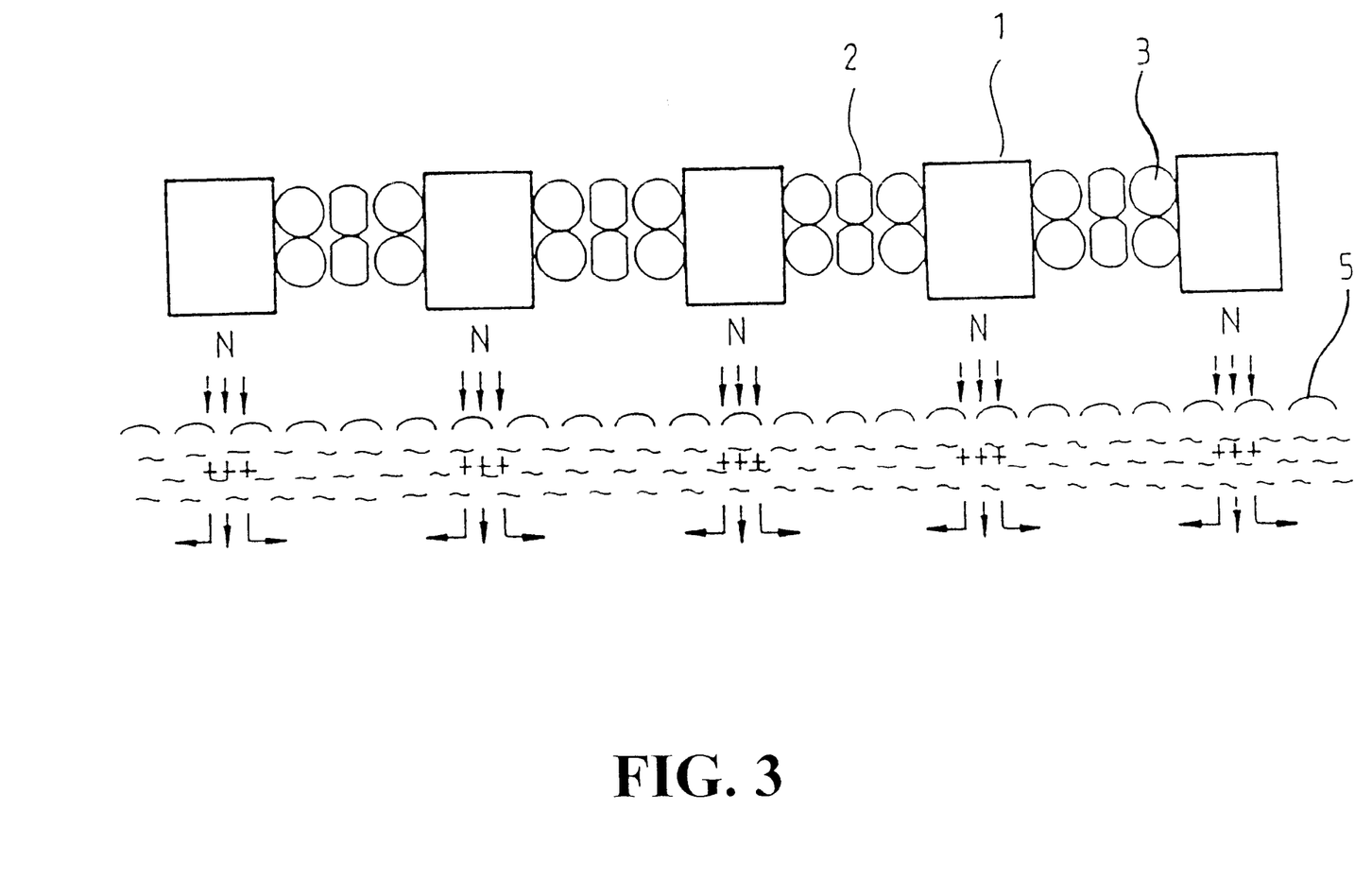
FIGS. 3 to 6 are schematic views illustrating different arrangements of the embodiments of the invention.

Referring to FIG. 3, during assembly of the invention, the superconductive magnetic materials 1 are elected to be red (yellow) and are so arranged to have the N polarity thereof oriented toward the surface of skin 5 of the user so as have a beneficial effect, i.e., to enhance vitality and rigor, and to promote health and body strength.

Figure 4:
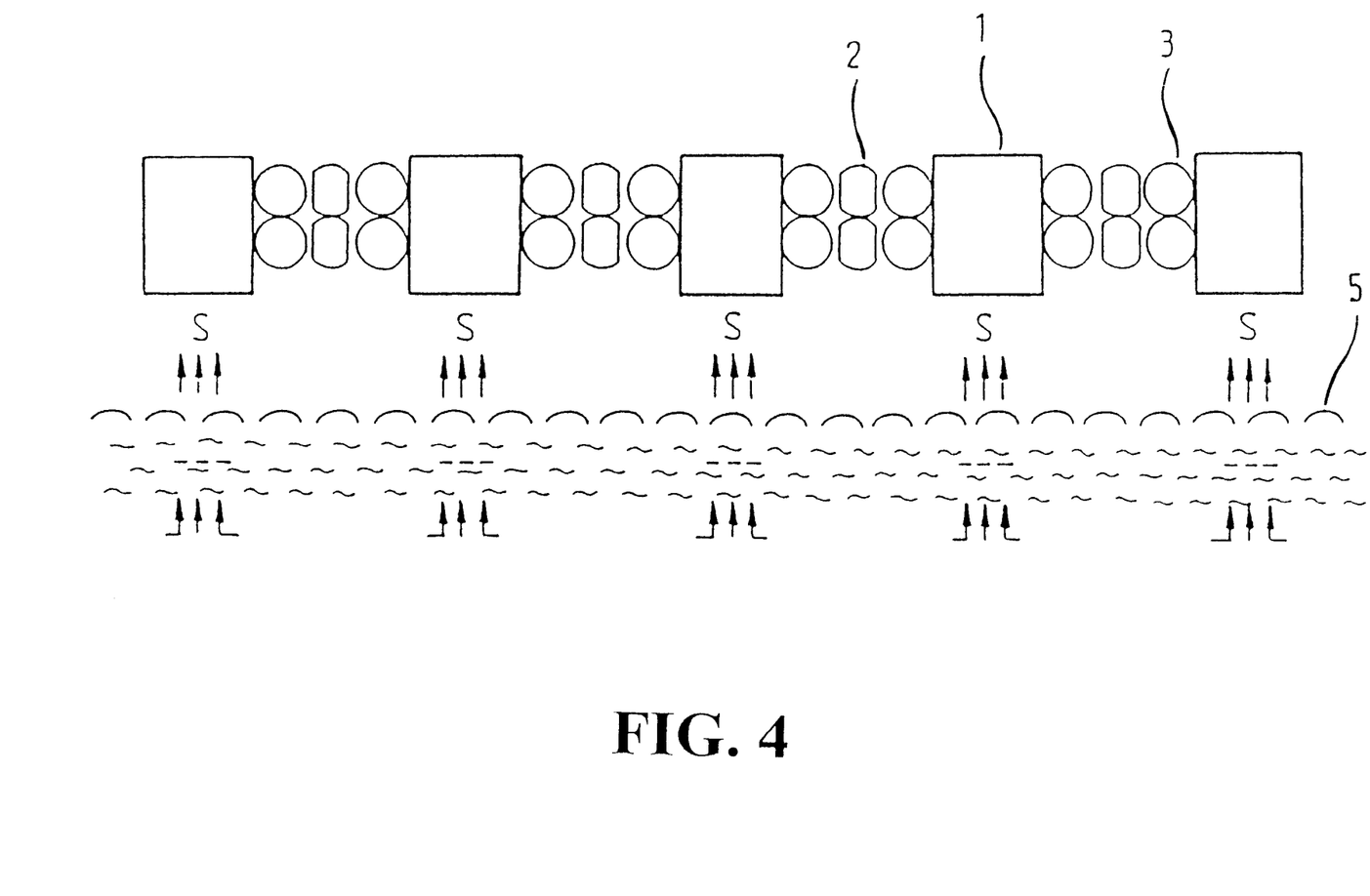

Referring to FIG. 4, a plurality of superconductive magnetic materials 1 of green (emerald green) color have the S polarity thereof oriented toward the surface of the skin 5 so as to have an "alternating nature," i.e., to be able to promote blood circulation and metabolism.

Figure 5:
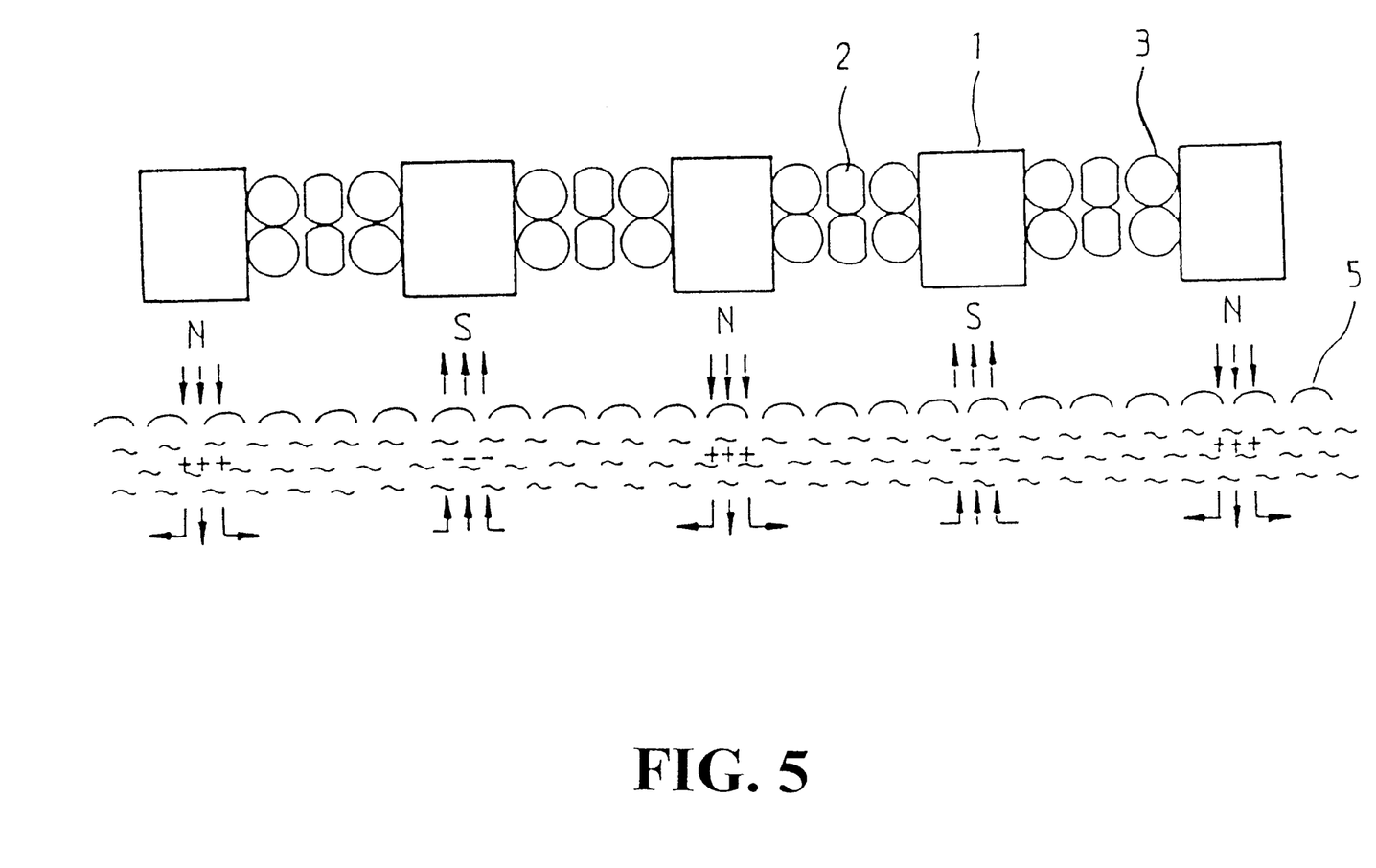
Figure 6:
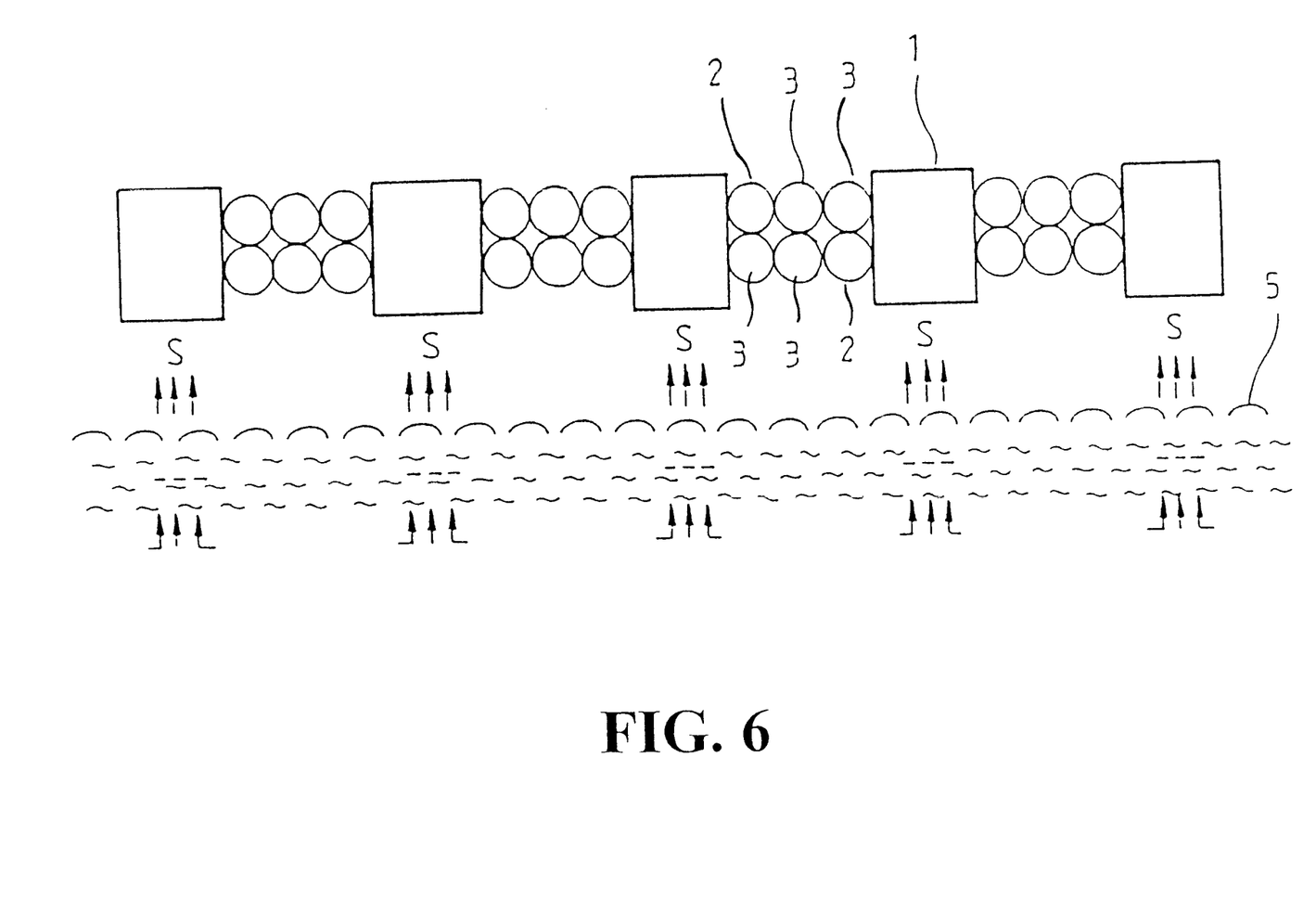

Referring to FIG. 5, the superconductive magnetic materials 1 of the invention can be set to have the color blue (black) and with the N and S polarities thereof oriented toward the surface of the skin 5 in an alternating manner so as to have a "channeling nature," i.e., to be able to relieve pressure, drain toxic substances, modulate and balance so that all parts of the body can function normally. If the natural crystals 2 are arranged in different positions, they can achieve a clockwise spiraling magnetic field with the superconductive magnetic materials 1 to enhance the magnetic field effect (see FIG. 6).

Figure 7:
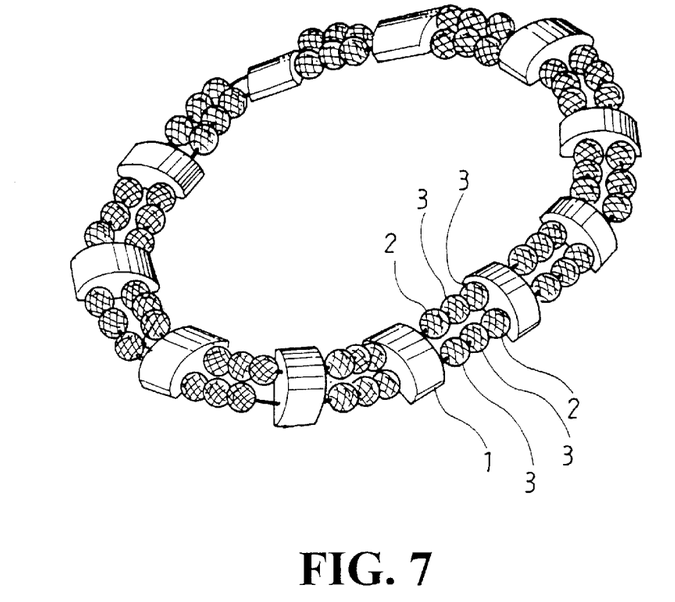
FIG. 7 is a schematic perspective view of another embodiment of the invention.
Figure 8:
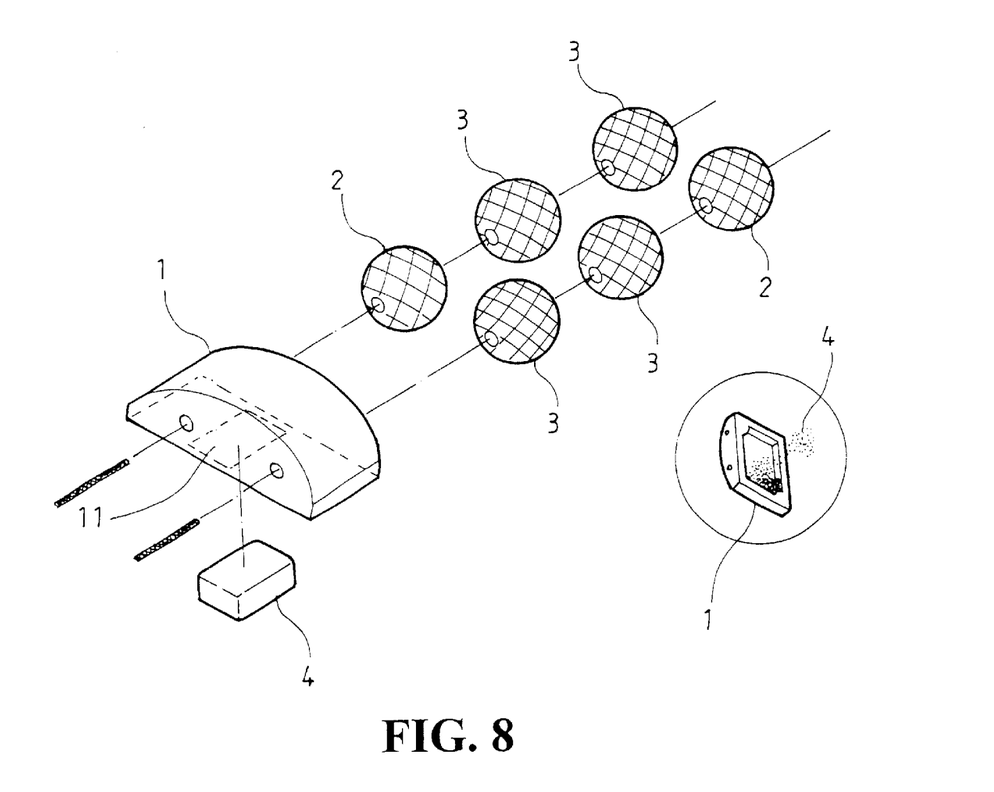
FIG. 8 is a schematic exploded view of FIG. 7.

Referring to FIGS. 7 and 8, the bottom portion of the superconductive magnetic materials 1 are provided with recesses 11 for embedding crude crystals 4, and the natural crystals 2 and ceramic beads 3 are configured to be round, with the crystals 2 arranged in a diagonally opposite positions. Due to the diagonal arrangement of the crystals 2 and the crude crystals 4 in the bottom portion, the magnetic ring thus assembled will form a whirling magnetic field to enhance the magnetic field effect.

Figure 9:
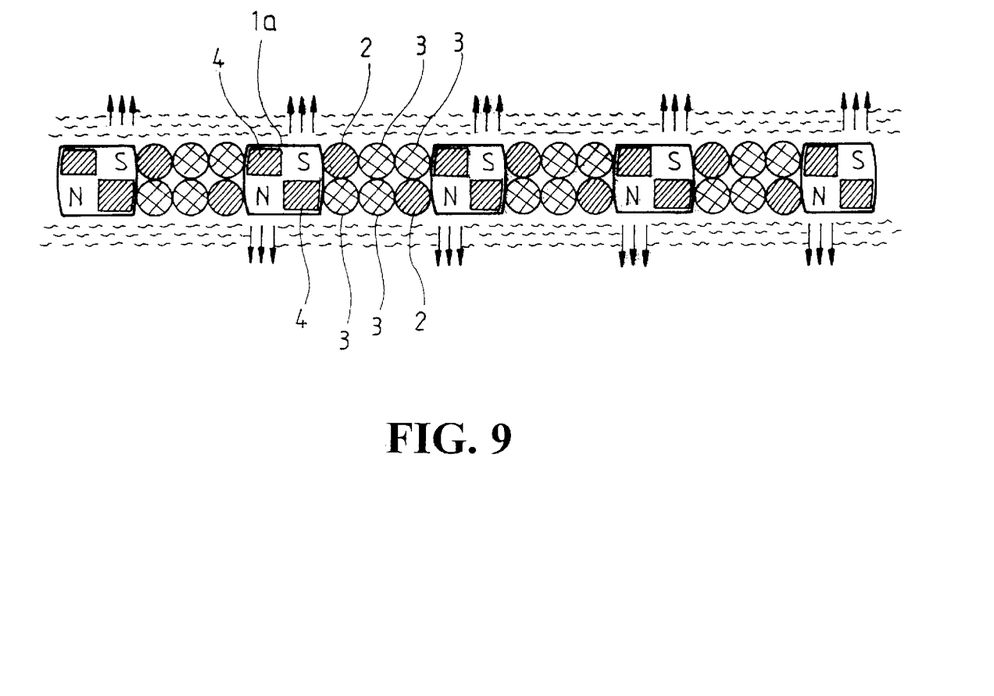
FIGS. 9 and 10 are schematic views illustrating different arrangements of another embodiment of the invention.
Figure 10:
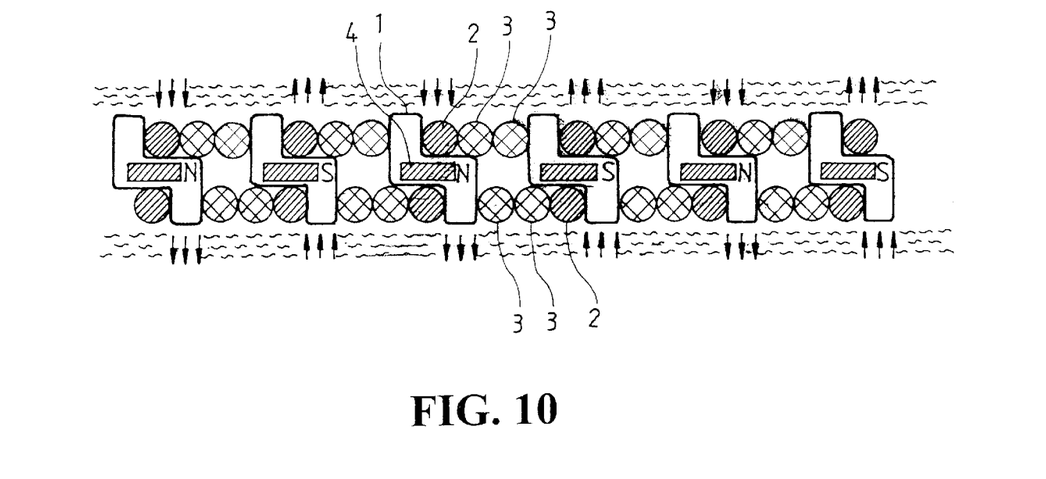

Referring to FIGS. 9 and 10, the superconductive magnetic materials 1 can be configured to be blocks 1a with curved edges or S-shaped blocks 1b, and the crude crystals 4 are arranged in the bottom portions thereof or in diagonally opposite positions, and the ceramic beads 3 and the natural crystals 2 are likewise arranged in diagonally opposite positions to thereby form another whirling effect and a different appearance.

Figure 11:
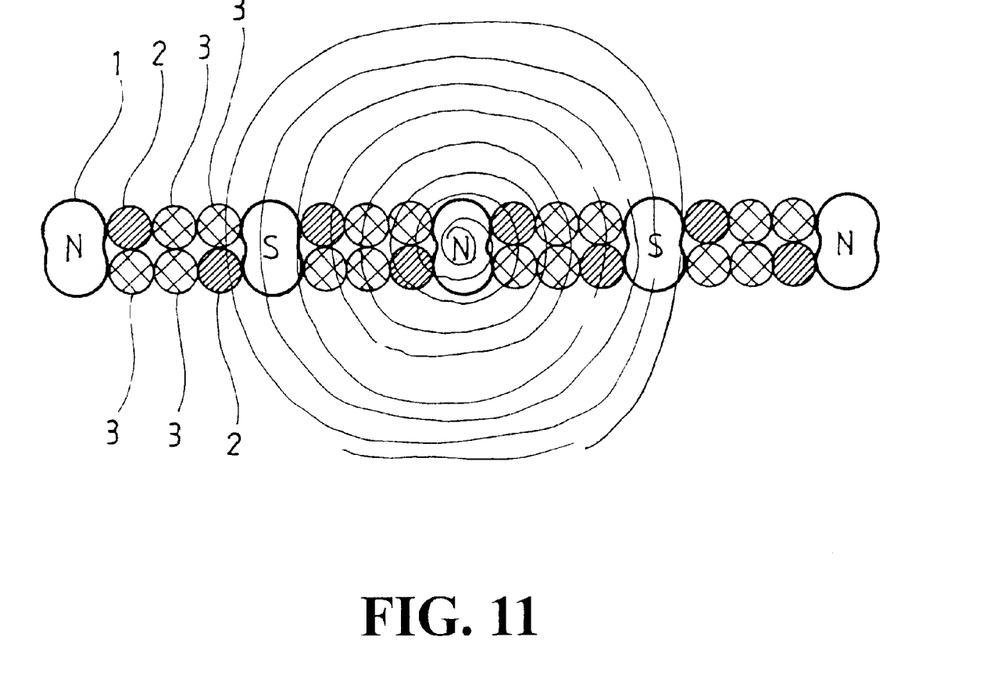
FIG. 11 is a schematic view illustrating a whirling magnetic field produced by the invention.

Referring to FIG. 11, the superconductive magnetic materials 1 are configured to be elliptical blocks 1c with upper and lower curves and slightly indented central portions and having bottom portions having crude crystals 4 embedded therein to produce a whirling magnetic field so as to enhance the magnetic field effect.

Figure 12:
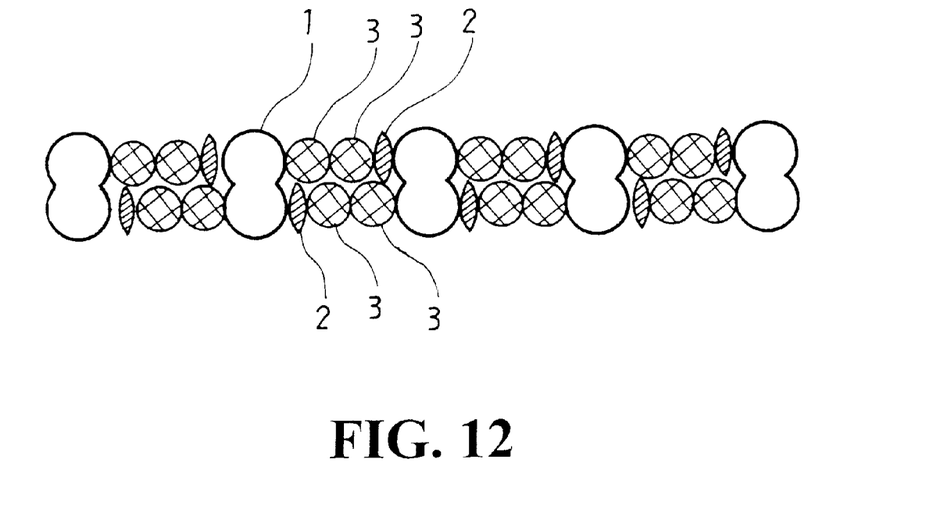
FIG. 12 is a schematic view illustrating a different shape of the natural crystals used in the invention.

Referring to FIG. 12, the crystals 2 can be configured to have a flat circular shape to obtain similar enhanced magnetic field effect and a magnetic field of a different shape.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A light wave energy health magnetic ring, comprising a plurality of blocks formed from superconductive magnetic materials of different colors, the blocks having bottom portions provided with recesses for embedding crude crystals, two natural crystals being arranged between adjacent superconductive magnetic materials, two ceramic beads being disposed on both sides of the crystal to sandwich the same, an elastic string passing through these elements to connect the same in a ring shape for wearing by a user.

2. The light wave energy magnetic ring as claimed in claim 1, wherein the superconductive magnetic materials are round and curved blocks, square-shaped blocks, S-shaped blocks, or elliptical-shaped blocks.

3. The light wave energy magnetic ring as claimed in claim 1, wherein the superconductive magnetic materials are red crystals, yellow crystals, green crystals, emerald green crystals, blue crystals or black crystals.

4. The light wave energy magnetic ring as claimed in claim 1, wherein the crude crystals embedded in the bottom portions of the superconductive magnetic materials are disposed in the center or upper and lower diagonally opposite positions of the superconductive magnetic materials.

5. The light wave energy magnetic ring as claimed in claim 1, wherein the natural crystals disposed between the superconductive magnetic materials are wheel-shaped or flat, circular-shaped.

6. The light wave energy magnetic ring as claimed in claim 1, wherein the natural crystals arranged between the superconductive magnetic materials are arranged side by side or in diagonally opposite positions.

* * * * *